W. P. Ware.
Ear, Cheek and Chin Muff.
No. 2,482. Reissued Feb. 12, 1867.
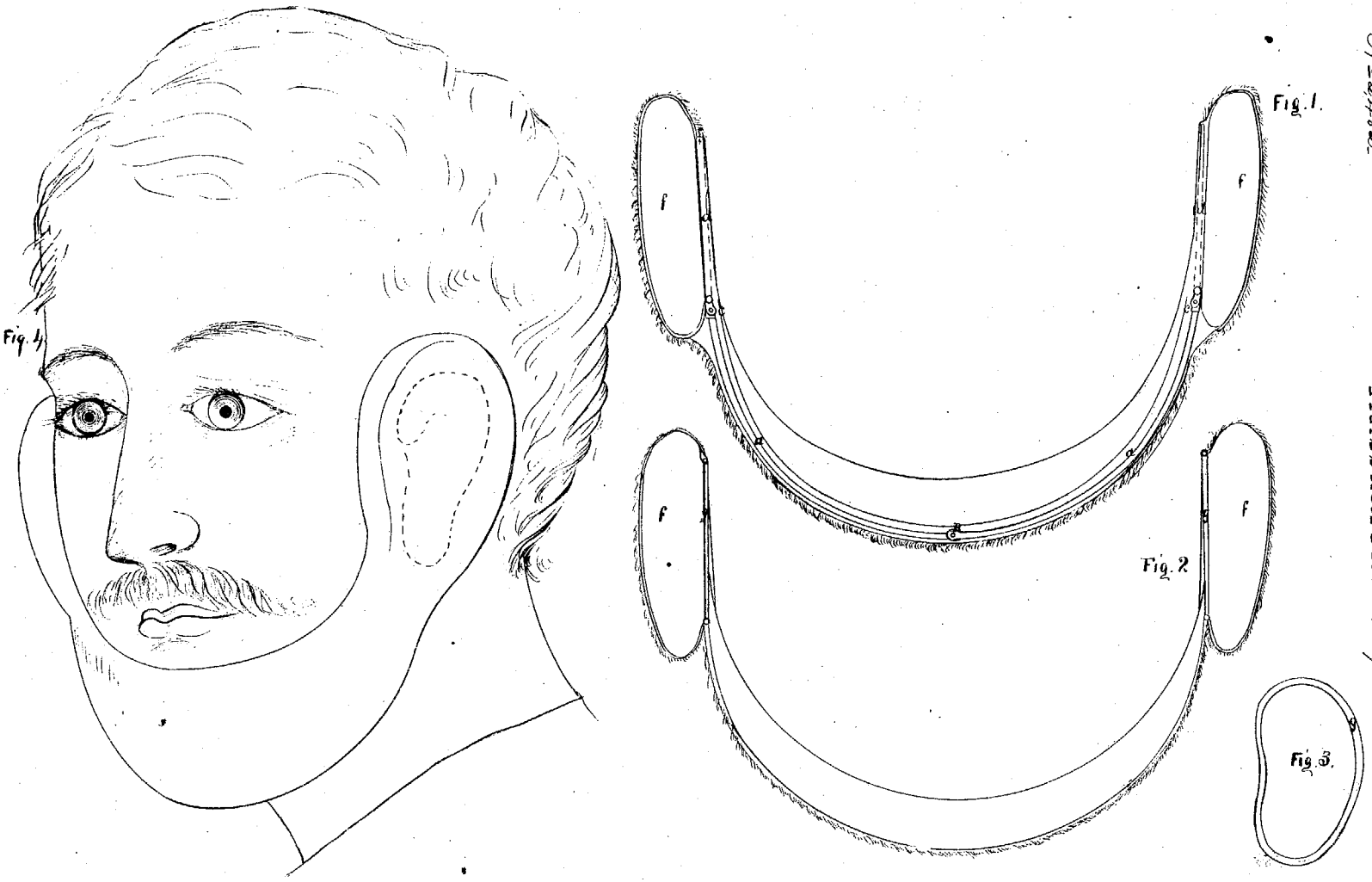

United States Patent Office.

WILLIAM P. WARE, OF CINCINNATI, OHIO.

*Letters Patent No.* 20,834, *dated July* 6, 1858; *reissue No.* 2,482, *dated February* 12, 1867.

IMPROVEMENT IN EAR, CHEEK, AND CHIN MUFFS.

The Schedule referred to in these Letters Patent and making part of the same.

TO ALL WHOM IT MAY CONCERN:

Be it known that I, WILLIAM P. WARE, formerly of the city of Cincinnati, in the county of Hamilton, and State of Ohio, have invented a new and useful improvement in what I denominate an Improved Muff for the Ears, Cheeks, or Chin; and I do hereby declare that the following is a full, clear, and exact description thereof, reference being had to the accompanying drawings, making part of this specification, and to the letters of reference marked thereon, in which similar letters refer to like parts.

The object of my improvement is to protect the ears, cheek, or chin from cold, without attaching or tying the muff or article used over the top of the head or around the neck and face, as is commonly done; and the nature of the improvement consists in what I denominate muffs or pockets for the ear, formed with rings or frames of wire or other material, to set around the base of the ears, and covered with fur or other substances, of such a size, shape, or fullness as to form a pocket containing the ears and protecting them from the cold. Said ear muffs also support and hold the cheek and chin muffs to their respective parts when connected with such ear muffs.

To enable others skilled in the art to make and use the improvement, I will proceed to describe its construction and use.

Figure 1 is a sectional view of an improved muff, showing the pockets and a frame of wire, and jointed for folding, and to which the muffing material or fur is attached.

Figure 2 is a similar view of a muff, without the frame of wire from ear to ear, as represented in fig. 1; but rings are used, as represented in Figure 3, to assist in forming the ear pockets; and Figure 4 represents a head, showing the mode of applying the muff.

*a a* is a frame of wire, jointed at B under the chin, and *c c* at the lower part of the ear pockets, for folding the muff up, to make it as portable as possible. *d d* are the ring portions of the muff frame, to which the pockets *f f* are attached, for containing the ears; and the frame is covered with fur in this case, but can be covered with cloth or any other material, if desired; and when the muff is used the pockets are placed over the ears, which hold the other portion of the muff to the cheeks and chin, as fully represented in fig. 1. Fig. 2 represents a muff made without the wire frame around the cheeks and chin; but rings, *g g*, are used in forming the pockets *f f*, and the cheek and chin portions of the muff extend from one ear muff to the other, and the article is to be worn as shown in fig. 1.

What I claim, and desire to secure by Letters Patent, is—

1. A muff or pocket for the ear, formed so as to surround the base of the ear, and extending of a size and shape to contain the ear and protect the same from cold, substantially as set forth.

2. I claim a cheek and chin muff, suspended from the ears substantially as specified, instead of being fastened around the neck or over the head.

3. I claim muffs or pockets formed to set over the ears, and held in place by a connection passing down under the chin, substantially as shown.

Dated this fifth day of January, A. D. 1867.

WM. P. WARE.

Witnesses:

CHAS. H. SMITH,

GEO. T. PINCKNEY.